United States Patent
Yamaguchi et al.

(10) Patent No.: US 6,903,237 B2
(45) Date of Patent: Jun. 7, 2005

(54) ECTOPARASITIC INSECT PEST CONTROLLERS FOR ANIMALS AND THEIR USAGE

(75) Inventors: Rikio Yamaguchi, Kawachinagano (JP); Tetsuyoshi Nishimatsu, Kawachinagano (JP); Kazuhiro Takagi, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 10/399,327

(22) PCT Filed: Oct. 16, 2001

(86) PCT No.: PCT/JP01/09076

§ 371 (c)(1),
(2), (4) Date: May 21, 2003

(87) PCT Pub. No.: WO02/32226

PCT Pub. Date: Apr. 25, 2002

(65) Prior Publication Data

US 2003/0199579 A1 Oct. 23, 2003

(30) Foreign Application Priority Data

Oct. 18, 2000 (JP) ......................................... 2000-317887

(51) Int. Cl.$^7$ ............................................. C07C 337/00
(52) U.S. Cl. ........................... 564/20; 564/34; 564/260; 514/590
(58) Field of Search ........................ 564/20, 34, 260; 514/590

(56) References Cited

U.S. PATENT DOCUMENTS 5,543,573 A * 8/1996 Takagi et al. ............... 514/590

FOREIGN PATENT DOCUMENTS

| EP | 0462456 | 12/1991 |
| EP | 0657421 | 6/1995 |
| JP | 5-32603 A | * 2/1993 |
| JP | 5-262712 A | * 10/1993 |
| WO | WO 01/01781 | 1/2001 |

OTHER PUBLICATIONS

Derwent Publications, AN 1994–012239, XP002262378 (JP 05 320116, Nihon Nohyaku Co. Ltd, Dec. 3, 1993).

* cited by examiner

Primary Examiner—Cecilia J. Tsang
Assistant Examiner—Hector M. Reyes

(74) Attorney, Agent, or Firm—Paul E. White, Jr.; Manelli Denison & Selter PLLC

(57) ABSTRACT

Ectoparasitic insect pest controllers for animals, containing hydrazine derivatives of the general formula (I) as the active ingredient, and methods for application of the same: (I) [wherein A is (II), (III), (IV), (V) (wherein $R^4$ and $R^5$ are each H, $C_{1-6}$ alkyl, or the like; and X is H, or one to five substituents selected from among halogeno and optionally halogenated $C_{1-6}$ alkyl groups); $R^1$ is H or $C_{1-6}$ alkyl; $R^2$ and $R^3$ are each H, OH, $C_{1-6}$ alkyl, phenylcarbonyl, or the like; Y is H, or one to five substituents selected from among halogeno, nitro, and cyano; Z is halogeno, cyano, $C_{1-6}$ alkyl, or the like; and W is O or S]. The insect pest controllers exert remarkable controlling effects on parasitic insect pests harmful to domestic or pet animals, e.g. fleas, lice, ticks.

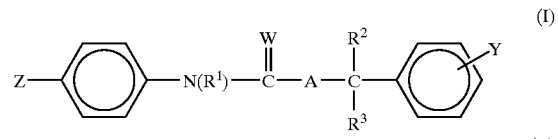

(I)

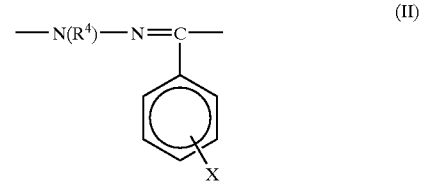

(II)

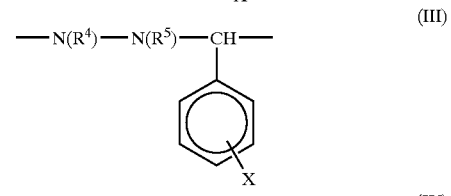

(III)

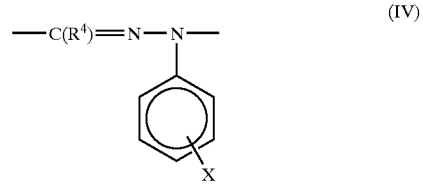

(IV)

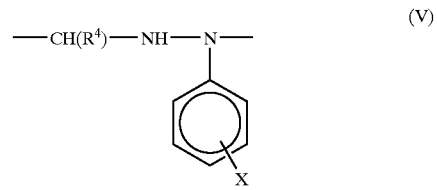

(V)

8 Claims, No Drawings

ECTOPARASITIC INSECT PEST CONTROLLERS FOR ANIMALS AND THEIR USAGE

TECHNICAL FIELD

This invention relates to novel ectoparasitic insect pest controllers for animals containing a hydrazine derivative as the active ingredient, and method for application of the same.

BACKGROUND ART

The hydrazine derivatives represented by the general formula (I) which are used as an active ingredient of the ectoparasitic insect pest controllers for animals of this invention are known compounds disclosed in JP-A-5-4958, JP-A-5-17428, JP-A-5-32603 and JP-A-5-262712, wherein is mentioned that these compounds, as an agrihorticultural insecticide, have a controlling effect on Lepidopterous insect pests such as diamondback moth (*Plutella xylostella* (Linnaeus)), rice leafroller (*Cnaphalocrosis medinalis* (Guenee)), etc.; Hemipterous insect pests such as tea green leafhopper (*Empoasca onukii* Matsuda), pear lace bug (*Stephanitis nashi* Esaki et Takeya), etc.; Coleopterous insect pests such as twenty-eight-spotted ladybird (*Epilachna vigintioctopunctata* (Fabricius)), maize weevil (*Sitophilus zeamais* Motschulsky), etc.; Dipterous insect pests such as melon fly (*Dacus* (Zeugodacus) *cucurbitae* Coquillett), muscid flies (Muscidae), *Culex pipiens molestus*, etc.; and tylenchid insect pests such as coffee root lesion nematode (*Pratylenchus coffeae* (Zimmermann) Filipjev et Schuurmans Stekhoven), root-knot nematode (*Meloidogyne* sp.), etc. However, in the above-mentioned prior arts, neither mention nor suggestion is made as to the insecticidal effect of these compounds on the ectoparasitic insect pests of animals such as insect pests belonging to fleas, lice and ticks.

A variety of chemicals have so far been proposed as an agent for controlling the ectoparasitic insect pests harmful to bred animals such as domestic and pet animals. However, an agent capable of exhibiting a high controlling effect on the ectoparasitic insect pests at a low dose is not yet known, and creation of such a novel agent is waited for.

The present inventors have conducted extensive studies with the aim of creating a novel agent exerting a remarkable controlling effect on the ectoparasitic insect pests of domestic and pet animals at a low dose. As a result, it has been found that some of the compounds selected from the hydrazine derivatives described in the above-mentioned prior arts have a remarkable controlling effect on the ectoparasitic insect pests of animals. Based on this finding, this invention has been accomplished.

DISCLOSURE OF THE INVENTION

This invention relates to an ectoparasitic insect pest controller for animals which contains, as active ingredient thereof, a hydrazine derivative represented by the following general formula (I):

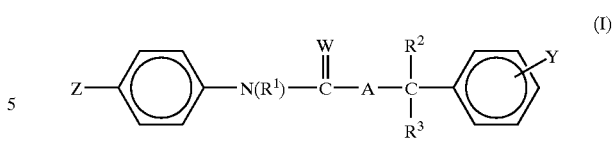

wherein A represents

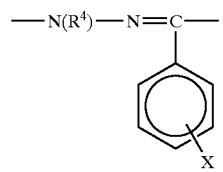

(in this formula, $R^4$ represents a hydrogen atom or a $C_{1-6}$alkyl group; X which may be the same or different represents one to five substituents selected from the group consisting of hydrogen atom, halogen atom, $C_{1-6}$alkyl group and halo $C_{1-6}$alkyl group);

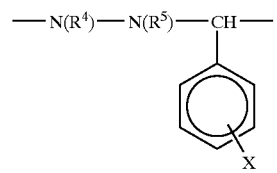

(in this formula, $R^4$ and X are as defined above, and $R^5$ represents a hydrogen atom, a $C_{1-6}$alkylcarbonyl group or a phenylcarbonyl group which may optionally have one or two, the same or different substituents selected from $C_{1-6}$alkyl groups);

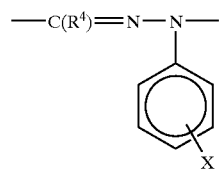

(in this formula, $R^4$ and X are as defined above), or

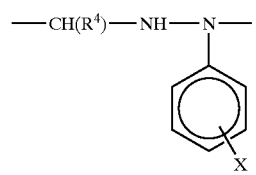

(in this formula, $R^4$ and X are as defined above);
  $R^1$ represents a hydrogen atom or a $C_{1-6}$alkyl group;
  $R^2$ and $R^3$ which may be the same or different, each represents a hydrogen atom, a hydroxyl group, a $C_{1-6}$alkyl group, a $C_{1-6}$alkoxy group, a $C_{1-6}$alkylcarbonyl group or a phenylcarbonyl group;
  Y which may be the same or different, represents one to five substituents selected from the group consisting of hydrogen atom, halogen atom, nitro group and cyano group;
  Z represents a halogen atom, a cyano group, a $C_{1-6}$alkyl group, a halo $C_{1-6}$alkyl group, a $C_{1-6}$alkoxy group, a halo $C_{1-6}$alkoxy group, a halo $C_{1-6}$alkylthio group, a halo $C_{1-6}$alkylsulfinyl group or a halo $C_{1-6}$alkylsulfonyl group; and W represents an oxygen atom or a sulfur atom; and to a method for using said insect pest controller.

The ectoparasitic insect pest controller for animals of this invention exerts a remarkable controlling effect on the parasitic insect pests harmful to domestic and pet animals, such as fleas, lice, ticks, etc.

BEST MODE FOR CARRYING OUT THE INVENTION

In the definition of the general formula (I) of this invention, "halogen atom" means chlorine atom, bromine atom, iodine atom or fluorine atom; "$C_{1-6}$alkyl" means a straight or branched chain alkyl group having 1–6 carbon atoms; and "halo $C_{1-6}$alkyl" means an alkyl group having 1–6 carbon atoms, substituted with at least one halogen atoms which may be the same or different. The hydrazine derivatives represented by the general formula (I) used as an active ingredient of the ectoparasitic insect pesst controller for animals of this invention can be produced according to the production processes mentioned in JP-A-5-4958, JP-A-5-17428, JP-A-5-32603 and JP-A-5-262712.

Among the hydrazine derivatives of this invention represented by the general formula (I), preferable are the hydrazine derivatives represented by the general formulas (I-1) and (I-2) and, in such preferable compounds, the substituent W is an oxygen atom, the substituent X is a trifluoromethyl group, the substituent Y is a cyano group, the substituent Z is a trifluoromethoxy group, and $R^1$, $R^2$, $R^3$ and $R^4$ simultaneously represent a hydrogen atom. As a further preferable compound, for example, (E)-2-[2-(4-cyanophenyl)-1-(3-trifluoromethylphenyl)ethylidene]-N-(4-trifluoromethoxyphenyl)hydrazine carboxamide can be referred to.

Next, typical examples of the hydrazine derivative represented by the general formula (I) which is an active ingredient of the ectoparasitic insect pest controller for animals of this invention will be shown in the following Tables 1 to 4. This invention, however, is not limited by these compounds. In the tables, Ph means a phenyl group.

TABLE 1

General formula (I-1)

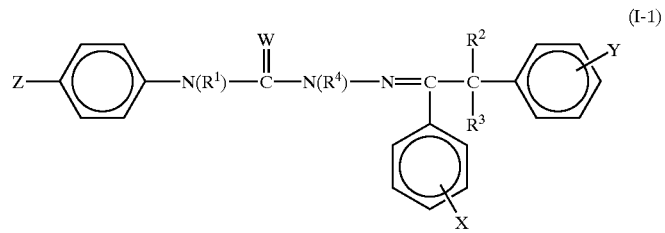

(I-1)

| No | $R^1$ | $R^2$ | $R^3$ | $R^4$ | X | Y | Z | W | mp° C. |
|---|---|---|---|---|---|---|---|---|---|
| 1 | H | H | H | H | H | H | Cl | O | 199 |
| 2 | H | H | H | H | H | H | $OCF_3$ | O | 149 |
| 3 | H | H | H | H | H | 4-Cl | Cl | O | 206 |
| 4 | H | H | H | H | H | 4-Cl | $OCF_3$ | O | 197 |
| 5 | H | H | H | H | H | 4-CN | Cl | O | 217 |
| 6 | H | H | H | H | H | 4-CN | Cl | S | 128 |
| 7 | H | H | H | H | H | 4-CN | $OCF_3$ | S | 116 |
| 8 | H | H | H | H | H | 4-CN | $OCF_3$ | O | 214 E-form |
| 9 | H | H | H | H | H | 4-CN | $OCF_3$ | O | 159 Z-form |
| 10 | H | H | H | H | H | 4-$NO_2$ | Cl | O | 222 |
| 11 | H | H | H | H | H | 4-$NO_2$ | Cl | S | 206 |
| 12 | H | H | H | H | H | 4-$NO_2$ | $OCF_3$ | O | 189 |
| 13 | H | H | H | H | H | 4-$NO_2$ | $OCF_3$ | S | 139 |
| 14 | H | H | H | H | H | 4-$NO_2$ | $SCF_3$ | O | 200 |
| 15 | H | H | H | H | 3-Cl | H | $OCF_3$ | O | 212 |
| 16 | H | H | H | H | 3-Cl | 4-Cl | $OCF_3$ | O | 201 |
| 17 | H | H | H | H | 3-Cl | 4-CN | Cl | O | 206 |
| 18 | H | H | H | H | 3-Cl | 4-CN | $OCF_3$ | O | 187 E-form |
| 19 | H | H | H | H | 3-Cl | 4-CN | $OCF_3$ | O | 148 Z-form |
| 20 | H | H | H | H | 3-Cl | 4-CN | $OCF_3$ | S | 199 |
| 21 | H | H | H | H | 3-Cl | 4-CN | $SCF_3$ | O | 215 |
| 22 | H | H | H | H | 3-Cl | 4-CN | $SOCF_3$ | O | 205 |
| 23 | H | H | H | H | 3-Cl | 4-CN | $SO_2CF_3$ | O | 212 |
| 24 | H | H | H | H | 3-Br | H | Cl | O | 191 |
| 25 | H | H | H | H | 3-Br | H | $OCF_3$ | O | 209 |
| 26 | H | H | H | H | 3-Br | 4-CN | Cl | O | 205 |
| 27 | H | H | H | H | 3-Br | 4-CN | $OCF_3$ | O | 176 |
| 28 | H | H | H | H | 3-Br | 4-CN | $SCF_3$ | O | 206 |
| 29 | H | H | H | H | 3-Br | 4-CN | $SOCF_3$ | O | 216 |
| 30 | H | H | H | H | 3-Br | 4-CN | $SO_2CF_3$ | O | 215 |
| 31 | H | H | H | H | 3-F | H | Cl | O | 206 |

TABLE 1-continued

General formula (I-1)

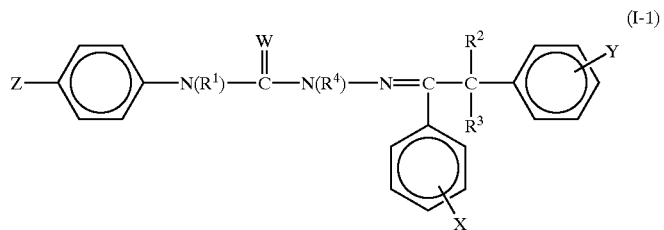

| No | R¹ | R² | R³ | R⁴ | X | Y | Z | W | mp° C. |
|---|---|---|---|---|---|---|---|---|---|
| 32 | H | H | H | H | 3-F | H | OCF₃ | O | 200 |
| 33 | H | H | H | H | 3-F | 4-Cl | OCF₃ | O | 191 |
| 34 | H | H | H | H | 3-F | 4-Cl | Cl | O | 208 |
| 35 | H | H | H | H | 3-F | 4-CN | OCF₃ | O | 202 |
| 36 | H | H | H | H | 3-I | 4-CN | Cl | O | 213 |
| 37 | H | H | H | H | 3-I | 4-CN | OCF₃ | O | 201 |
| 38 | H | H | H | H | 3-CH₃ | H | Cl | O | 185 |
| 39 | H | H | H | H | 3-CH₃ | H | OCF₃ | O | 198 |
| 40 | H | H | H | H | 3-CH₃ | 4-CN | Cl | O | 200 |
| 41 | H | H | H | H | 3-CH₃ | 4-CN | OCF₃ | O | 189 |
| 42 | H | H | H | H | 3-CF₃ | H | Cl | O | 206 |
| 43 | H | H | H | H | 3-CF₃ | H | OCF₃ | O | 210 |
| 44 | H | H | H | H | 3-CF₃ | 4-CN | OCF₃ | O | 191 |
| 45 | H | H | H | H | 3-CF₃ | 4-CN | OCF₃ | S | 149 |
| 46 | CH₃ | H | H | H | H | H | Cl | O | 132 |
| 47 | CH₃ | H | H | H | H | H | OCF₃ | O | 108 |
| 48 | H | CH₃ | H | H | H | H | Cl | O | 98 |
| 49 | H | CH₃ | H | H | H | H | Br | O | 85 |
| 50 | H | CH₃ | H | H | H | H | OCF₃ | O | 115 EZ-form |
| 51 | H | CH₃ | H | H | H | H | OCF₃ | O | 95 E-form |
| 52 | H | CH₃ | H | H | H | H | OCF₃ | O | 66 Z-form |
| 53 | H | CH₃ | H | H | H | 4-Cl | Cl | O | 121 |
| 54 | H | CH₃ | H | H | H | 4-Cl | OCF₃ | O | 105 |
| 55 | H | CH₃ | H | H | 3-Cl | 4-CN | Cl | O | 140 |
| 56 | H | CH₃ | H | H | 3-Cl | 4-CN | OCF₃ | O | 98 |
| 57 | H | H | OH | H | H | H | Cl | O | 188 |
| 58 | H | H | OH | H | H | H | OCF₃ | O | 170 |
| 59 | H | H | OH | H | H | 4-Cl | Cl | O | Viscous material |
| 60 | H | H | OH | H | H | 4-Cl | OCF₃ | O | 185 E-form |
| 61 | H | H | OH | H | H | 4-Cl | OCF₃ | O | 95 Z-form |
| 62 | H | H | OH | H | H | 4-CN | Cl | O | Viscous material |
| 63 | H | H | OH | H | H | 4-CN | OCF₃ | O | 113 |
| 64 | H | H | CH₃ | H | H | H | Cl | O | 164 |
| 65 | H | H | CH₃ | H | H | H | OCF₃ | S | 118 |
| 66 | H | H | OCH₃ | H | H | H | Cl | O | 183 |
| 67 | H | H | OCH₃ | H | H | H | OCF₃ | O | 181 |
| 68 | H | H | OC₃H₇-i | H | H | H | Cl | O | 155 |
| 69 | H | H | OC₃H₇-i | H | H | H | OCF₃ | O | 193 |
| 70 | H | H | OC₄H₉-i | H | H | H | Cl | O | 176 |
| 71 | H | H | OC₄H₉-i | H | H | H | OCF₃ | O | 184 |
| 72 | H | H | O—CO—CH₃ | H | H | H | OCF₃ | O | 182 |
| 73 | H | H | O—CO—Ph | H | H | H | OCF₃ | O | 168 |
| 74 | H | H | OH | CH₃ | H | H | Cl | O | 115 |
| 75 | H | H | OH | CH₃ | H | H | OCF₃ | O | 130 |
| 76 | H | H | H | H | 3-F | 4-CN | SCF₃ | O | 214 |
| 77 | H | H | H | H | 3-F | 4-CN | SOCF₃ | O | 214 |
| 78 | H | H | H | H | 4-F | 4-CN | SO₂CF₃ | O | 165 |
| 79 | H | H | H | H | 3-Cl | 4-CN | SOCF₃ | O | 157 |
| 80 | H | H | H | H | 3-CF₃ | 4-CN | SCF₃ | O | 215 |
| 81 | H | H | H | H | 3-CF₃ | 4-CN | SOCF₃ | O | 210 |
| 82 | H | H | H | H | 3-CF₃ | 4-CN | OCF₃ | O | 152 Z-form |
| 83 | H | H | H | H | 3-CF₃ | 4-CN | Cl | O | 165 |

TABLE 2

General Formula (I-2)

$$\text{(I-2)}$$

(R¹ and R³ are hydrogen atoms.)

| No | R² | R⁴ | R⁵ | X | Y | Z | W | mp° C. |
|---|---|---|---|---|---|---|---|---|
| 84 | H | H | H | H | H | Cl | O | 211 |
| 85 | H | H | H | H | H | OCF₃ | O | 194 |
| 86 | H | H | H | H | 4-Cl | OCF₃ | O | 209 |
| 87 | H | H | H | H | 4-CN | OCF₃ | O | 204 |
| 88 | H | H | H | H | 4-NO₂ | OCF₃ | O | 203 |
| 89 | H | H | H | 3-F | 4-Cl | OCF₃ | O | 203 |
| 90 | H | H | H | 3-Cl | 4-Cl | OCF₃ | O | 176 |
| 91 | H | H | H | 3-Cl | 4-CN | OCF₃ | O | 193 |
| 92 | H | H | H | 3-Cl | 4-CN | SCF₃ | O | 177 |
| 93 | H | H | H | 3-Cl | 4-CN | SOCF₃ | O | 178 |
| 94 | H | H | H | 3-Cl | 4-CN | SO₂CF₃ | O | 170 |
| 95 | H | H | H | 3-Br | 4-CN | OCF₃ | O | 187 |
| 96 | H | H | H | 3-CF₃ | 4-CN | OCF₃ | O | 165 |
| 97 | H | H | H | 3-CF₃ | 4-CN | SCF₃ | O | 164 |
| 98 | H | H | H | H | 4-Cl | OCF₃ | S | 171 |
| 99 | H | H | H | 3-Cl | 4-CN | OCF₃ | S | 149 |
| 100 | H | H | H | 3-CF₃ | 4-CN | OCF₃ | S | 209 |
| 101 | H | H | CO—CH₃ | 3-Cl | 4-CN | OCF₃ | O | 178 |
| 102 | H | H | CO—Ph | 3-Cl | 4-CN | OCF₃ | O | 221 |
| 103 | H | H | CONHC₂H₅ | 3-Cl | 4-CN | OCF₃ | O | 201 |
| 104 | H | OH | H | H | H | OCF₃ | O | 190 |
| 105 | H | OCH₃ | H | H | H | Cl | O | 195 |
| 106 | H | OCH₃ | H | H | H | OCF₃ | O | 183 |
| 107 | H | OCH₃ | H | H | H | OCF₃ | O | 186 |
| 108 | CH₃ | H | H | 3-Cl | 4-CN | OCF₃ | O | 156 |
| 109 | H | H | H | H | 4-F | OCF₃ | O | 209 |
| 110 | H | H | H | H | 4-Br | Cl | O | 233 |
| 111 | H | H | H | H | 4-Br | OCF₃ | O | 201 |
| 112 | H | H | H | H | 3-CN | OCF₃ | O | 176 |
| 113 | H | H | H | H | 2-NO₂ | OCF₃ | O | 197 |
| 114 | H | H | H | 3-F | 4-CN | OCF₃ | O | 189 |
| 115 | H | H | H | 3-F | 4-CN | SCF₃ | O | 189 |
| 116 | H | H | H | 3-F | 4-CN | SOCF₃ | O | 166 |
| 117 | H | H | H | 3-CF₃ | 4-CN | OCF₃ | O | 131 −Isomer |
| 118 | H | H | H | 3-CF₃ | 4-CN | OCF₃ | O | 126 +Isomer |
| 119 | H | H | H | 3-CF₃ | 4-CN | SOCF₃ | O | Glassy material |
| 120 | H | H | H | 3-CF₃ | 4-CN | SO₂CF₃ | O | Glassy material |
| 121 | H | H | H | H | 3-CN | OCF₃ | O | 120 |

Notes: In this table, Ph represents a phenyl group. Compound Nos. 106 and 107 are diastereomers. Compound No. 106 is higher than Compound No. 107 in Rf value.

TABLE 3

General formula (I-3)

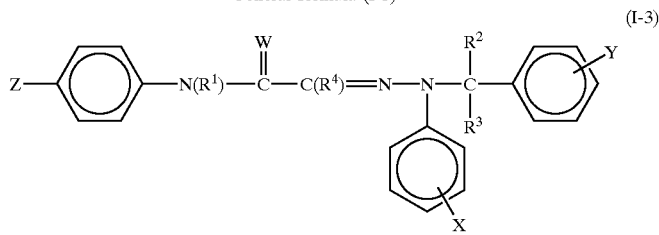

(I-3)

(In this table, $R^2$ and $R^3$ are hydrogen atoms, and W is an oxygen atom.)

| No | $R^1$ | $R^4$ | X | Y | X | mp° C. Refractive index |
|---|---|---|---|---|---|---|
| 122 | H | H | H | H | $OCF_3$ | 113.3–114.0 |
| 123 | H | H | H | 4-Cl | $OCF_3$ | 137.8 |
| 124 | H | H | H | 4-CN | Cl | 163 |
| 125 | H | H | H | 4-CN | $OCF_3$ | 138 |
| 126 | H | H | 3-Cl | 4-Cl | Cl | 143.5–144.0 |
| 127 | H | H | 3-Cl | 4-Cl | $OCF_3$ | 139.6–141.5 |
| 128 | H | H | 3-Cl | 4-$NO_2$ | Cl | 174.0–176.5 |
| 129 | H | H | 3-Cl | 4-$NO_2$ | $OCF_3$ | 151.6–151.7 |
| 130 | H | H | 3-Cl | 4-CN | Cl | 191.0–192.0 |
| 131 | H | H | 3-Cl | 4-CN | $OCF_3$ | 160.5–162.0 |
| 132 | H | H | 3-Cl | 4-CN | $SCF_3$ | 188.0 |
| 133 | H | H | 3-Cl | 4-CN | $SOCF_3$ | 206.1 |
| 134 | H | H | 3-F | 4-CN | Cl | 154–156 |
| 135 | H | H | 3-F | 4-CN | $OCF_3$ | 155.9–156.8 |
| 136 | H | H | 3-$CH_3$ | 4-CN | Cl | 127 |
| 137 | H | H | 3-$CH_3$ | 4-CN | $OCF_3$ | 166 |
| 138 | H | H | 3-$CF_3$ | 4-CN | Cl | 164–165 |
| 139 | H | H | 3-$CF_3$ | 4-CN | $OCF_3$ | 151.0 |
| 140 | H | $CH_3$ | 3-Cl | 4-CN | $OCF_3$ | nD 1.5950(25° C.) |
| 141 | $CH_3$ | H | 3-$CF_3$ | 4-CN | Cl | 209–211 |
| 142 | H | H | 3-Cl | 2-CN | $OCF_3$ | 148 |

TABLE 4

General formula (I-4)

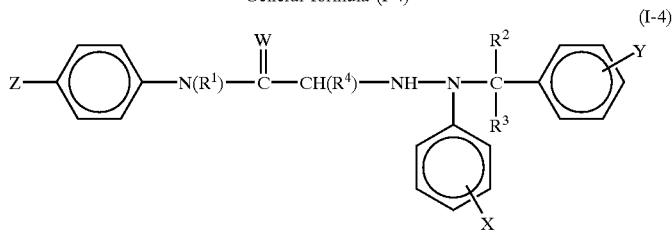

(I-4)

(In this formula, $R^1$, $R^2$, $R^3$ and $R^4$ are hydrogen atoms, and W is an oxygen atom.)

| No | X | Y | Z | mp° C. Refractive index |
|---|---|---|---|---|
| 143 | H | H | $OCF_3$ | 51.0–53.0 |
| 144 | H | 4-Cl | $OCF_3$ | 92.1 |
| 145 | H | 4-CN | Cl | 106–108 |
| 146 | H | 4-CN | $OCF_3$ | nD 1.5685 (27° C.) |
| 147 | 3-Cl | 4-Cl | Cl | 105.3–106.4 |
| 148 | 3-Cl | 4-Cl | $OCF_3$ | 38.0 |
| 149 | 3-Cl | 4-$NO_2$ | Cl | Viscous material |
| 150 | 3-Cl | 4-$NO_2$ | $OCF_3$ | Viscous material |
| 151 | 3-Cl | 4-CN | Cl | 153.1 |
| 152 | 3-Cl | 4-CN | $OCF_3$ | 43.5–45.0 |
| 153 | 3-F | 4-CN | Cl | 164–165 |
| 154 | 3-F | 4-CN | $OCF_3$ | nD 1.5615 (27° C.) |
| 155 | 3-$CH_3$ | 4-CN | Cl | 138–139 |

TABLE 4-continued

General formula (I-4)

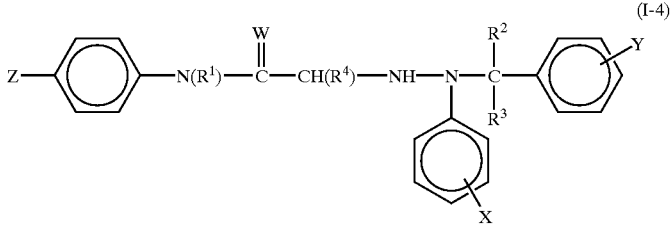

(I-4)

(In this formula, $R^1$, $R^2$, $R^3$ and $R^4$ are hydrogen atoms, and W is an oxygen atom.)

| No | X | Y | Z | mp° C. Refractive index |
|---|---|---|---|---|
| 156 | 3-$CH_3$ | 4-CN | $OCF_3$ | nD 1.5315 (28° C.) |
| 157 | 3-$CF_3$ | 4-CN | Cl | 43 |
| 158 | 3-$CF_3$ | 4-CN | $OCF_3$ | 153.1 |

Some of the compounds shown in Tables 1 to 4 are viscous substances or glassy substances. $^1$H-NMR date of these compounds are shown in Table 5.

| No | $^1$H-NMR [$CDCl_3$/TMS, δ value (ppm)] |
|---|---|
| 59 | 6.29(s, 1H), 7.65–7.92(m, 13H), 9.14(bs, 1H), 10.70(bs, 1H). (DMSO-$d_6$) |
| 62 | 3.88(bs, 1H), 3.87(s, 1H), 6.91–7.55(m, 13H), 7.73(s, 1H), 8.13(bs, 1H). |
| 119 | 3.12(dd, 1H), 3.23(dd, 1H), 4.12–4.32(m, 2H), 6.13(bs, 1H), 7.24–7.93(m, 12H), 8.08(bs, 1H). |
| 120 | 3.11(dd, 1H), 3.23(dd, 1H), 4.13–4.28(m, 2H), 5.97(s, 1H), 7.25–7.75(m, 12H), 7.90–8.00(bs, 1H). |
| 149 | 3.65(d, 2H), 4.20(t, 1H), 4.70(s, 2H), 6.85(dd, 1H), 6.93(dd, 1H), 7.08(dd, 1H), 7.15–7.21 (m, 3H), 7.24(d, 2H), 7.40(d, 2H), 8.13(d, 2H), 8.40 (s, 1H). |
| 150 | 3.64(s, 2H), 4.69(s, 2H), 6.84(dd, 1H), 6.94 (dd, 1H), 7.09(m, 3H), 7.23(t, 1H), 7.29(d, 2H), 7.40(d, 2H), 8.12(d, 2H), 8.40(s, 1H). |

The ectoparasitic insect pest controller for animals of this invention can be used for domestic animals such as cattle, horse, sheep, etc.; and pets such as dog, cat, etc.; as well as for Rodential animals such as mouse, rat, hamster, squirrel, etc.; Lagomorphous animals, Carnivorous animals such as ferret, etc.; and birds such as duck, chicken, pigeon, etc. As the ectoparasitic pest insects of these animals, for example, the insects belonging to fleas such as

| | |
|---|---|
| cat flea | (Ctenocephalides felis), |
| dog flea | (Ctenocephalides canis), |
| oriental rat flea | (Xenopsylla cheopis), etc.; the insects belonging to ticks such as |
| Haemaphysalis longicornis, | |
| cattle tick | (Boophilus microplus), etc.; and the insects belonging to lice such as |
| cattle louse | (Haematopinus eurysternus), |
| sheep louse | (Damalinia ovis), etc. can be referred to. |

For an effective use of the ectoparasitic insect pest controllers for animals of this invention represented by the general formula (1), the controller is compounded with an appropriate solid carrier and/or liquid carrier and, if necessary, adjuvants and the like in an appropriate proportion according to the conventional recipe in the drug making and fixed on the carriers by dissolution, suspension, mixing, impregnation, adsorption or adhesion. The resulting mixture is formed into an appropriate preparation form such as liquid preparation, emulsion, cream, ointment, suspension, aerosol, etc. according to the purpose of the use, and then the formed preparation is put to use.

The solid or liquid carriers used in this invention may be the carriers conventionally used for agents for animals. From the viewpoint of easiness of treatment on the objective animals, the use of liquid carriers is preferable. As examples of the liquid carrier, alcohols such as methyl alcohol, ethyl alcohol, isopropyl alcohol, tertiary butyl alcohol, benzyl alcohol and the like; propylene carbonate; N-methyl-2-pyrrolidone; water, etc. can be referred to.

According to the need, adjuvants can be incorporated into the controller of this invention. As the adjuvants, surfactants, antioxidants, emulsifiers, etc. can be referred to. More specific examples of the adjuvants include surfactants such as polyoxyethylene alkylaryl ether, polyoxyethylene sorbitan monolaurate, alkylaryl sorbitan monolaurate, alkylbenzenesulfonates, alkylnaphthalene-sulfonic acid, ligninsulfonic acid salts, higher alcohol sulfate salts, glycol monoalkyl ethers, glycols, and the like; emulsifiers such as sorbitan monooleate, sorbitan monolaurate, caprylic acid monoglyceride, capric acid monoglyceride, isostearic acid monoglyceride, propylene glycol monocaprylate, etc; and antioxidants such as BHA, BHT, etc.

The ectoparasitic insect pest controller composition for animals of this invention can contain the insect pest controller of this invention as an active ingredient in an amount of 0.01–80.0% by weight per 100 parts by weight of the present composition.

The methods for using the ectoparasitic insect pest controller for animals of this invention include a pot-on treatment which comprises dropping a liquid agent onto the skin of the back shoulder region of the objective animal and thereby controlling the ectoparasitic insect pest; and a local treatment such as pore-on which comprises applying a liquid agent along the back center line of the objective animal and the allowing the applied agent to diffuse on the body surface and thereby controlling the ectoparasitic insect pest; as well as a treatment method of supporting the agent on a collar or the like from which the agent is released; a treatment method of directly coating a liquid agent or an ointment onto the body surface; a treatment method of applying an aerosol of a liquid agent by means of spray or the like; etc. The dose of the agent may be appropriately selected from a range of about 0.1 to 500 mg as expressed in terms of active ingredient compound, and from a range of about 0.01 to 20 ml as expressed in terms of the insect pest controller of this invention, both per kilogram of body weight of the objective animal.

According to the need, the ectoparasitic insect pest controller for animals of this invention may be used in combination with other active ingredients. As said "other active ingredient", for example, the following can be referred to:

pyrethroid compounds such as permethrin, phenothrin, allethrin, pyrethrin, prallethrin, cyphenothrin, cyfluthrin, fenvalerate, fenpropathrin, transfluthrin, etc.;

organic phosphorus compounds such as dichlorvos, tetrachlorvinphos, fenthion, chlorpyrifos, diazinon, etc.;

N-phenylpyrazole compounds such as fipronil, etc.;

carbamate compounds such as propoxur, carbaryl, metoxadiazone, fenocarb, etc.;

neonicotinoid compounds; etc.

EXAMPLES

Example 1

| A compound shown in Tables 1–4 | 5 parts |
| Hexylene glycol | 50 parts |
| Isopropanol | 45 parts |

The above-mentioned ingredients were uniformly mixed and dissolved together to obtain a liquid formulation.

Example 2

| A compound shown in Tables 1–4 | 10 parts |
| Polyoxyethylene styrylphenyl ether | 10 parts |
| Cylohexanone | 80 parts |

The above-mentioned ingredients were uniformly mixed and dissolved together to obtain an emulsifier.

Test Example 1

A spot-on agent was prepared by mixing and dissolving 10 parts by weight of Compound 44 or Compound 96 in 90 parts by weight of diethylene glycol monoethyl ether. One day before the day of administration, 30 fleas [adult worm of cat flea (*Ctenocephalides felis*)] were made to parasitize a cat, and the cat was let wear an Elizabeth collar on the neck. Then, 0.4 ml of a test agent was applied to the skin of back shoulder area of the cat (alive body weight 3.2 kg). One day after and three days after the treatment using the agent, the number of parasitic fleas was counted by means of a flea-catching comb. After counting the number of parasitic fleas, the whole fleas were again made to parasitize the cat. As a blank test, fleas were made to parasitize an untreated cat in the same manner as above, and the number of parasitic fleas was counted. The controlling rate was calculated according to the following formula, and the result was judged according to the criterion shown below.

$$\text{Controlling rate } (\%) = \frac{\text{Parasitic rate in untreated group} - \text{Parasitic rate in treated group}}{\text{Parasitic rate in untreated group}} \times 100$$

| Criterion of judgement | Controlling rate (%) |
|---|---|
| A | 100 |
| B | 99–90 |
| C | 89–80 |
| D | 79–50 |

Thus, both the ectoparasitic insect pest controllers for animals containing Compound No. 44 and Compound No. 96 of this invention gave a judgement of A.

What is claimed is:

1. A method of controlling ectoparasitic insect pests for animals which comprises the steps of administering an effective amount of a controller to the body surface of an animal, which contains, as active ingredient thereof, a hydrazine derivative represented by the following general formula (I):

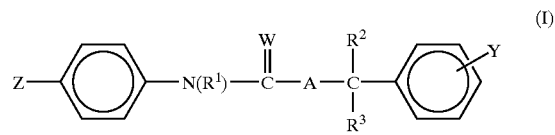

wherein A represents

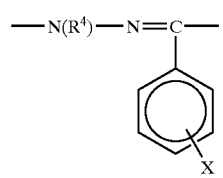

in this formula, $R^4$ represents a hydrogen atom or a $C_{1-6}$ alkyl group; X which may be the same or different represents one to five substituents selected from the group consisting of hydrogen atom, halogen atom, $C_{1-6}$ alkyl group and halo $C_{1-6}$ alkyl group;

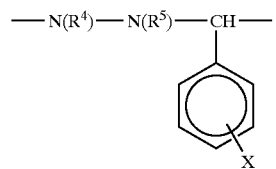

in this formula, $R^4$ and X are as defined above, and $R^5$ represents a hydrogen atom, a $C_{1-6}$ alkylcarbonyl group or a phenylcarbonyl group which may optionally have one or two, the same or different substituents selected from $C_{1-6}$ alkyl groups;

—C(R⁴)=N—N—

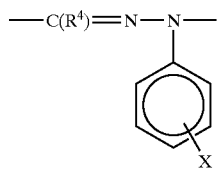

in this formula, R⁴ and X are as defined above, or

—CH(R⁴)—NH—N—

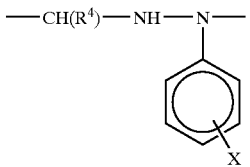

in this formula, R⁴ and X are as defined above;

R$^1$ represents a hydrogen atom or a C$_{1-6}$ alkyl group;

R$^2$ and R$^3$ which may be the same or different, each represents a hydrogen atom, a hydroxyl group, a C$_{1-6}$ alkyl group, a C$_{1-6}$ alkoxy group, a C$_{1-6}$ alkylcarbonyl group or a phenylcarbonyl group;

Y which may be the same or different, represents one to five substituents selected from the group consisting of hydrogen atom, halogen atom, nitro group and cyano group;

Z represents a halogen atom, a cyano group, a C$_{1-6}$ alkyl group, a halo C$_{1-6}$ alkyl group, a C$_{1-6}$ alkoxy group, a halo C$_{1-6}$ alkoxy group, a halo C$_{1-6}$ alkylthio group, a halo C$_{1-6}$ alkylsulfinyl group or a halo C$_{1-6}$ alkylsulfonyl group; and W represents an oxygen atom or a sulfur atom.

2. The method of controlling ectoparasitic insect pests for animals according to claim 1, represented by the following general formula (I-1):

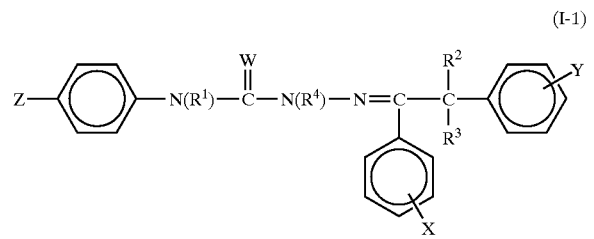

(I-1)

wherein R$^1$ represents a hydrogen atom or a C$_{1-6}$ alkyl group; R$^2$ and R$^3$ which may be the same or different, each represents a hydrogen atom, a hydroxyl group, a C$_{1-6}$ alkyl group, a C$_{1-6}$ alkoxy group, a C$_{1-6}$ alkylcarbonyl group or a phenylcarbonyl group; R$^4$ represents a hydrogen atom or a C$_{1-6}$ alkyl group; X which may be the same or different represents 1–5 substituents selected from the group consisting of hydrogen atom, halogen atom, C$_{1-6}$ alkyl group and halo C$_{1-6}$ alkyl group; Y which may be the same or different represents 1–5 substituents selected from the group consisting of hydrogen atom, halogen atom, nitro group and cyano group; Z represents a halogen atom, a cyano group, a C$_{1-6}$ alkyl group, a halo C$_{1-6}$ alkyl group, a C$_{1-6}$ alkoxy group, a halo C$_{1-6}$ alkoxy group, a halo C$_{1-6}$ alkylthio group, a halo C$_{1-6}$ alkylsulfinyl group or a halo C$_{1-6}$ alkylsulfonyl group; and W represents an oxygen atom or a sulfur atom.

3. The method of controlling ectoparasitic insect pests for animals according to claim 1, represented by the following general formula (I-2):

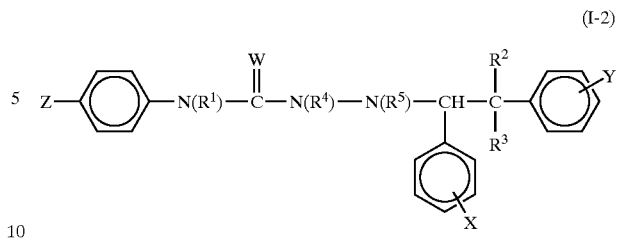

(I-2)

wherein R$^1$ represents a hydrogen atom or a C$_{1-6}$ alkyl group; R$^2$ and R$^3$ which may be the same or different, each represents a hydrogen atom, a hydroxyl group, a C$_{1-6}$ alkyl group, a C$_{1-6}$ alkoxy group, a C$_{1-6}$ alkylcarbonyl group or a phenylcarbonyl group; R$^4$ represents a hydrogen atom or a C$_{1-6}$ alkyl group; R$^5$ represents a hydrogen atom, a C$_{1-6}$ alkylcarbonyl group or a phenylcarbonyl group which may optionally have one or two, the same or different substituents selected from C$_{1-6}$ alkyl groups; X which may be the same or different represents 1–5 substituents selected from the group consisting of hydrogen atom, halogen atom, C$_{1-6}$ alkyl group and halo C$_{1-6}$ alkyl group; Y which may be the same or different represents 1–5 substituents selected from the group consisting of hydrogen atom, halogen atom, nitro group and cyano group; Z represents a halogen atom, a cyano group, a C$_{1-6}$ alkyl group, a halo C$_{1-6}$ alkyl group, a C$_{1-6}$ alkoxy group, a halo C$_{1-6}$ alkoxy group, a halo C$_{1-6}$ alkylthio group, a halo C$_{1-6}$ alkylsulfinyl group or a halo C$_{1-6}$ alkylsulfonyl group; and W represents an oxygen atom or a sulfur atom.

4. The method of controlling ectoparasitic insect pests for animals according to claim 1, represented by the following general formula (I-3):

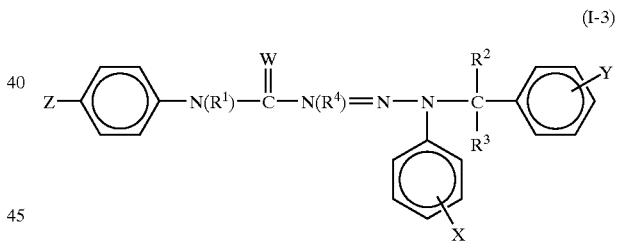

(I-3)

wherein R$^1$ represents a hydrogen atom or a C$_{1-6}$ alkyl group; R$^2$ and R$^3$ which may be the same or different, each represents a hydrogen atom, a hydroxyl group, a C$_{1-6}$ alkyl group, a C$_{1-6}$ alkoxy group, a C$_{1-6}$ alkylcarbonyl group or a phenylcarbonyl group; R$^4$ represents a hydrogen atom or a C$_{1-6}$ alkyl group; X which may be the same or different represents 1–5 substituents selected from the group consisting of hydrogen atom, halogen atom, C$_{1-6}$ alkyl group and halo C$_{1-6}$ alkyl group; Y which may be the same or different represents 1–5 substituents selected from the group consisting of hydrogen atom, halogen atom, nitro group and cyano group; Z represents a halogen atom, a cyano group, a C$_{1-6}$ alkyl group, a halo C$_{1-6}$ alkyl group, a C$_{1-6}$ alkoxy group, a halo C$_{1-6}$ alkoxy group, a halo C$_{1-6}$ alkylthio group, a halo C$_{1-6}$ alkylsulfinyl group or a halo C$_{1-6}$ alkylsulfonyl group; and W represents an oxygen atom or a sulfur atom.

5. The method of controlling ectoparasitic insect pests for animals according to claim 1, represented by the following general formula (I-4):

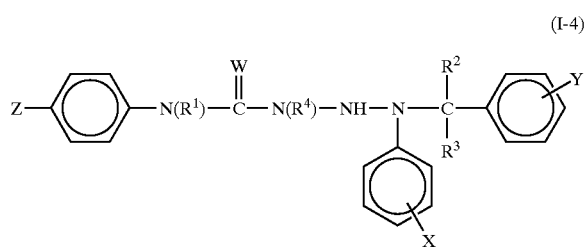

(I-4)

wherein $R^1$ represents a hydrogen atom or a $C_{1-6}$ alkyl group; $R^2$ and $R^3$ which may be the same or different, each represents a hydrogen atom, a hydroxyl group, a $C_{1-6}$ alkyl group, a $C_{1-6}$ alkoxy group, a $C_{1-6}$ alkylcarbonyl group or a phenylcarbonyl group; $R^4$ represents a hydrogen atom or a $C_{1-6}$ alkyl group; X which may be the same or different represents 1–5 substituents selected from the group consisting of hydrogen atom, halogen atom, $C_{1-6}$ alkyl group and halo $C_{1-6}$ alkyl group; Y which may be the same or different represents 1–5 substituents selected from the group consisting of hydrogen atom, halogen atom, nitro group and cyano group; Z represents a halogen atom, a cyano group, a $C_{1-6}$ alkyl group, a halo $C_{1-6}$ alkyl group, a $C_{1-6}$ alkoxy group, a halo $C_{1-6}$ alkoxy group, a halo $C_{1-6}$ alkylthio group, a halo $C_{1-6}$ alkylsulfinyl group or a halo $C_{1-6}$ alkylsulfonyl group: and W represents an oxygen atom or a sulfur atom.

6. The method of controlling ectoparasitic insect pests for animals according to claim 1, wherein the active ingredient is present in an amount of 0.01–80.0% by weight.

7. The method of controlling ectoparasitic insect pests for animals according to claim 1, wherein the effective amount is a dose of 0.1 to 500 mg per kilogram of body weight of the animal.

8. The method of controlling ectoparasitic insect pests for animals according to claim 7, wherein the controller includes a liquid carrier and the dose is in an amount of 0.01 to 20 ml of the controller applied per kilogram of body weight of the animal.

* * * * *